United States Patent [19]

Tsang

[11] Patent Number: 5,837,442
[45] Date of Patent: Nov. 17, 1998

[54] OLIGONUCLEOTIDE PRIMERS FOR AMPLIFYING HCV NUCLEIC ACID

[75] Inventor: Sue Yen Tsang, Walnut Creek, Calif.

[73] Assignee: Roche Molecular Systems, Inc., Branchburg, N.J.

[21] Appl. No.: 738,928

[22] Filed: Oct. 28, 1996

Related U.S. Application Data

[60] Provisional application No. 60/007,739 Nov. 29, 1995.

[51] Int. Cl.$^6$ .............................. C12Q 1/70; C12Q 1/68; C12P 29/34; C07H 21/04
[52] U.S. Cl. .................................. 435/5; 435/6; 435/91.2; 435/810; 536/24.32; 536/24.33; 935/8; 935/11; 935/77; 935/78
[58] Field of Search .................................. 435/5, 6, 91.2, 435/810; 536/24.32, 24.33; 935/8, 11, 77, 78

[56] References Cited

U.S. PATENT DOCUMENTS 5,527,669  6/1996  Resnick et al. .............................. 435/5

OTHER PUBLICATIONS

Choo et al., Mar., 1991, "Genetic Organization and Diversity of the Hepatitis C Virus" *Proc. Natl. Acad. Sci. USA* 88:2451–2455.

Young et al., Apr., 1993, "Detection of Hepatitis C Virus RNA by a Combined Reverse Transcription–Polymerase Chain Reaction Assay" *J. Clinical Microbiology* 31(4):882–886.

Young et al., Mar., 1995, "Detection of Hepatitis C Virus RNA by a Combined Reverse Transcription PCR Assay: Comparision with Nested Amplification and Antibody Testing" J. Clinical Microbiology 33(3):654–657.

Simmonds, Feb., 1995, "Variability of Hepatitic C Virus" *Hepatology* 21(2):570–583.

Kleter et al, Journal of Medical Virology (1995) 47: 35–42.

Stuyver et al, Journal of General Virology (1993) 74: 1093–1102.

Schlauder et al, Journal of Virological Methods (1992) 37: 189–200.

*Primary Examiner*—Carla J. Myers
*Attorney, Agent, or Firm*—George W. Johnston; Dennis P. Tramaloni; Doug Petry

[57] ABSTRACT

The present invention provides improved primers for the polymerase chain reaction (PCR) amplification of a nucleic acid sequence from hepatitis C virus (HCV). The primers and amplification methods of the invention enable the detection of HCV with greatly increased sensitivity.

17 Claims, 3 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GCAGAAAGCG TCTAGCCATG GCGTTA            2 6

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCAAGCACCC TATCAGGCAG TACCACAA          2 8

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

(x i) SEQUENCE DESCRIPTION: SEQ ID NO:3:

GCAAGCACCC TATCAGGCAG TACCACA 27

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:4:

GCAGAAAGCG TCTAGCCATG GCGT 24

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:5:

CTCGCAAGCA CCCTATCAGG CAGT 24

OLIGONUCLEOTIDE PRIMERS FOR AMPLIFYING HCV NUCLEIC ACID

This application claims priority to U.S. provisional application No. 60/007,739, filed Nov. 29, 1995.

BACKGROUND OF THE INVENTION

1. Field of the Invention

The present invention relates to the field of molecular biology and nucleic acid chemistry. More specifically, it relates to methods and reagents for amplifying hepatitis C virus (HCV) nucleic acid. The invention therefore has applications in the detection of HCV, the field of medical diagnostics generally, and the field of molecular biology.

2. Description of Related Art

The Hepatitis C virus is a small RNA virus containing a single, positive sense, molecule of RNA about 10,000 nucleotides in length. The prototypical HCV was described in Choo et al., 1989, Science 244:359–362; Choo et al., 1991, Proc. Natl. Acad. Sci. USA 88:2451–2455; and European Patent Publication Nos. 318,216; 388,232; and 398,748. The genome is believed to contain a single, long, open reading frame that is translated into a single, large polyprotein and subsequently processed. The genome is known to contain a 5' untranslated region (UTR) upstream of the open reading frame.

The genome of HCV exhibits a large degree of nucleic acid sequence heterogeneity among strains and isolates (see Simmonds, 1995, Hepatology 21:570–583, and Bukh et al., 1994, Proc. Nati. Acad. Sci. USA 91:8239–8243, both incorporated herein by reference). The 5' UTR sequence, however, is known to be relatively conserved.

The invention of the polymerase chain reaction (PCR), a method for amplifying specific sequences of nucleic acids, makes possible the rapid detection of nucleic acids present in a sample in what was previously an undetectably low quantity (see U.S. Pat. Nos. 4,683,195; 4,683,202; and 4,965,188, each of which is incorporated herein by reference). HCV genomic RNA can be detected by reverse transcribing HCV genomic RNA to form cDNA, amplifying the resulting cDNA by PCR, and detecting the presence of amplified product.

HCV detection assays based on PCR amplification of HCV genomic sequences were described in copending U.S. patent application Ser. No. 08/240,547, now allowed; European Patent Publication No. 529,493; Young et al., 1993, J. Clin. Microbiol. 31(4):882–886; and Young et al., 1995, J. sin. Microbiol. 33(3):654–657, each incorporated herein by reference. As described therein, amplification of HCV RNA can be carried out using a combined reverse transcription-polymerase chain reaction (RT-PCR) amplification, in which a single enzyme catalyzes the primer extension both from the initial genomic RNA template (i.e., reverse transcription) and from the DNA templates synthesized in the amplification process.

SUMMARY OF THE INVENTION

The present invention provides improved oligonucleotide primers for the efficient reverse transcription-polymerase chain reaction (RT-PCR) amplification of a region of the 5' untranslated region of the hepatitis C virus (HCV) genome.

An important advantage of the primers of the present invention over primers described in the prior art is that the present primers enable amplification of HCV nucleic acid with significantly higher efficiency. As shown in the examples, amplifications of HCV nucleic acid using the primers of the present invention are up to a 100-fold more efficient than amplifications using the primers described in the prior art. The significantly greater amplification efficiency obtained using the primers of the present invention is surprising and unexpected in view of the prior art.

Another aspect of the invention relates to methods for amplifying a region of the HCV genome which comprise carrying out a polymerase chain reaction using the primers of the invention. Because of the significantly enhanced amplification efficiency obtained using the primers of the present invention, the amplification methods of the present invention provide significantly more amplified product while reducing the amount of primer-dimer formed. As a consequence, the methods of the present invention enable significantly more sensitive HCV detection assays. Thus, the present invention also provides methods for detecting the presence of HCV nucleic acid in a sample comprising:

(a) treating said sample in a PCR reaction mixture containing the primers of the present invention under amplification conditions so that HCV nucleic acid, if present, is amplified; and (b) detecting if amplification has occurred, which indicates that HCV nucleic acid is present.

Another aspect of the invention relates to kits which contain the amplification primers of the invention. These kits can include additional reagents, such as oligonucleotide probes for the detection of the amplified nucleic acid, and one or more amplification reagents, e.g., polymerase, buffers, and nucleoside triphosphates.

DETAILED DESCRIPTION OF THE INVENTION

Figure 1:
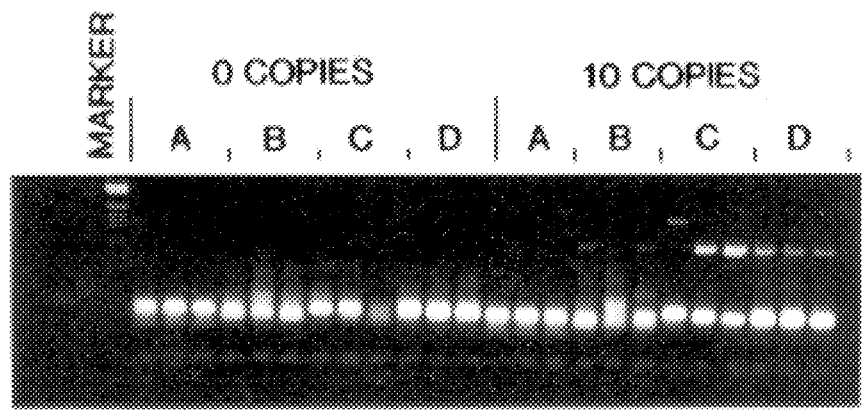
FIG. 1 provides the results of the amplifications described in Example 2. The top panel provides the results of amplifications using 0 and 10 copies of target. The bottom panel provides the results of amplifications using 25 and 100 copies of target.
Figure 1:
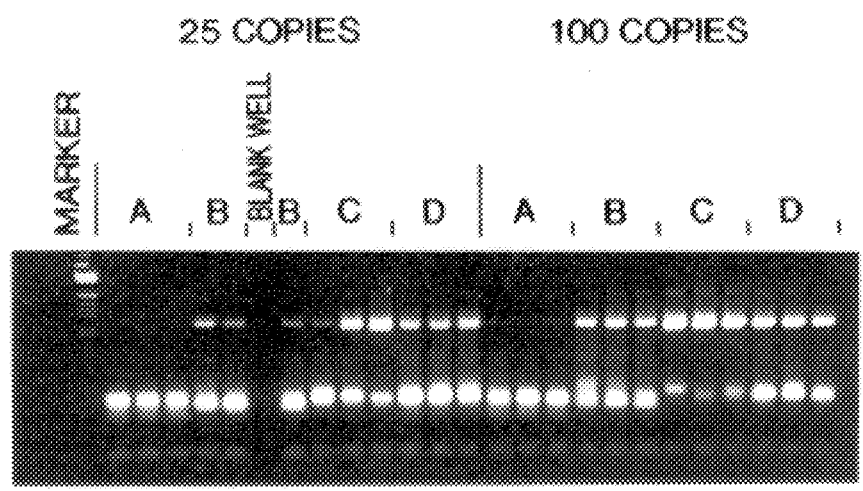

To aid in understanding the invention, several terms are defined below.

The terms "nucleic acid" and "oligonucleotide" refer to primers, probes, and oligomer fragments to be amplified or detected, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA.

Oligonucleotides can be prepared by any suitable method, including, for example, cloning and restriction of appropriate sequences and direct chemical synthesis by a method such as the phosphotriester method of Narang et al., 1979, Meth. Enzyrol. 68:90–99; the phosphodiester method of Brown et al., 1979, Meth. Enzymol. 68:109–151; the diethylphosphoramidite method of Beaucage et al., 1981, Tetrahedron Lett. 22:1859–1862; and the solid support method of U.S. Pat. No. 4,458,066, each incorporated herein by reference. Methods for synthesizing labeled oligonucleotides are described in Agrawal and Zamecnik, 1990, *Nucl. Acids. Res.* 18(18):5419–5423; MacMillan and Verdine, 1990, *J. Org. Chem.* 55:5931–5933; Pieles et al, 1989, *Nucl. Acids. Res.* 17(22):8967–8978; Roget et al., 1989,*Nucl. Acids. Res.* 17(19):7643–7651;and Tesler et al., 1989, *J. Am. Chem. Soc.* 111:6966–6976, each incorporated herein by reference. A review of synthesis methods is provided in Goodchild, 1990, *Bioconiulate Chemistry* 1(3):165–187, incorporated herein by reference.

The term "hybridization" refers to the formation of a duplex structure by two single-stranded nucleic acids due to complementary base pairing. Hybridization can occur between fully (exactly) complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions. Those skilled in the art of nucleic acid technology can determine duplex stability empirically following the guidance provided by the art (see, e.g., Sambrook et al., 1985, Molecular Cloning—A Laboratory Manual, Cold Spring Harbor Laboratory, Cold Spring Harbor, N.Y., incorporated herein by reference).

Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Relaxing the stringency of the hybridization conditions will allow sequence mismatches to be tolerated; the degree of mismatch tolerated can be controlled by suitable adjustment of the hybridization conditions.

The term "primer" refers to an oligonucleotide capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template. A primer need not reflect the exact sequence of the template nucleic acid, but must be sufficiently complementary to hybridize with the template. Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning of the amplified product. The region of the primer which is sufficiently complementary to the template to hybridize is referred to herein as the hybridizing region.

As used herein, an "upstream" primer refers to a primer whose extension product is a subsequence of the coding strand; a "downstream" primer refers to a primer whose extension product is a subsequence of the complementary non-coding strand. A primer used for reverse transcription, referred to as an "RT primer", hybridizes to the coding strand and is thus a downstream primer.

The term "oligonucleotide probe", as used herein, refers to a oligonucleotide which forms a duplex structure with a sequence of a target nucleic acid due to complementary base pairing. Probes are used for the detection or capture of the target nucleic acid. A probe is preferably a single-stranded oligodeoxyribonucleotide. The probe typically will consist of, or contain, a "hybridizing region" consisting preferably of from 10 to 50 nucleotides, more preferably from 15 to 35 nucleotides, corresponding to a region of the target sequence. "Corresponding" means at least substantially complementary to either the designated nucleic acid or its complement. A probe need not reflect the exact sequence of the target nucleic acid, but must be sufficiently complementary to hybridize with the target under the hybridization conditions chosen. A probe oligonucleotide can contain, or be bound to, additional features which allow for the detection or immobilization of the probe but do not significantly alter the hybridization characteristics of the hybridizing region. For example, probes may be labeled by the incorporation of radiolabeled nucleotides or by being bound to a separate detectable moiety.

As used herein, an oligonucleotide primer or probe is "specific" for a target sequence if the number of mismatches present between the oligonucleotide and the target sequence is less than the number of mismatches present between the oligonucleotide and non-target sequences. Hybridization conditions can be chosen under which stable duplexes are formed only if the number of mismatches present is no more than the number of mismatches present between the oligonucleotide and the target sequence. Under such conditions, the target-specific oligonucleotide can form a stable duplex only with a target sequence. The use of target-specific primers under suitably stringent amplification conditions enables the specific amplification of those target sequences which contain the target primer binding sites. Similarly, the use of target-specific probes under suitably stringent hybridization conditions enables the detection of a specific target sequence.

The terms "target region" and "target nucleic acid" refers to a region of a nucleic acid which is to be amplified, detected, or otherwise analyzed. The sequence to which a primer or probe hybridizes can be referred to as a "target".

The term "thermostable DNA polymerase" refers to an enzyme that is relatively stable to heat and catalyzes the polymerization of nucleoside triphosphates to form primer extension products that are complementary to one of the nucleic acid strands of the target sequence. The enzyme initiates synthesis at the 3' end of the primer and proceeds in the direction toward the 5' end of the template until synthesis terminates. Purified thermostable DNA polymerases are commercially available from Perkin-Elmer, Norwalk, Conn.

The terms "amplification reaction mixture" and "polymerase chain reaction mixture" refer to a combination of reagents that is suitable for carrying out a polymerase chain reaction. The reaction mixture typically consists of oligonucleotide primers, nucleotide triphosphates, and a DNA polymerase in a suitable buffer. Preferred amplification reaction mixtures are provided in the examples.

The term "amplification conditions", as used herein, refers to reaction conditions suitable for the amplification of the target nucleic acid sequence. The amplification conditions refers both to the amplification reaction mixture and to the temperature cycling conditions used during the reaction.

Under amplification conditions using the primers of the present invention, amplification of HCV nucleic acid, if present, will occur. Preferred amplification conditions are provided in the examples.

The term "amplification efficiency", as used herein, refers to the amount of product produced from a given initial number of target sequences in a given number of amplification cycles. Thus, the amplification efficiencies of two reaction which differ only in the primers used are compared by quantitatively measuring the amount of product formed in each reaction.

Conventional techniques of molecular biology and nucleic acid chemistry, which are within the skill of the art, are fully explained in the literature. See, for example, Sambrook et al., 1989, *Molecular Cloning—A Laboratory Manual,* Cold Spring Harbor Laboratory, Cold Spring Harbor, N.Y.; *Oligonucleotide Synthesis* (M. J. Gait, ed., 1984); *Nucleic Acid Hybridization* (B. D. Hames and S. J. Higgins. eds., 1984); and a series, *Methods in Enzynology* (Academic Press, Inc.), all of which are incorporated herein by reference. All patents, patent applications, and publications mentioned herein, both supra and infra, are incorporated herein by reference.

HCV Amplification Primers

The nucleotide sequences of the primers are provided in Table 1, shown in the 5' to 3' orientation. Amplifications using the upstream primer with either of the downstream primers amplify a 240 base pair product from the 5' untranslated region of the HCV genome. The primers hybridize to relatively conserved regions within the 5' untranslated region of the HCV genome and enable the amplification of nucleic acid from the known HCV isolates without the simultaneous amplification of non-target sequences from other viruses or from human genomic DNA.

TABLE 1

HCV Amplification Primers

| Upstream | Seq. ID No. | |
|---|---|---|
| ST280A | 1 | 5'-GCAGAAAGCGTCTAGCCATGGCGTTA |
| Downstream (RT) | | |
| ST778AA | 2 | 5'-GCAAGCACCCTATCAGGCAGTACCACAA |
| ST678A | 3 | 5'-GCAAGCACCCTATCAGGCAGTACCACA |

Amplification

The polymerase chain reaction (PCR) amplification process is well known in the art and described in U.S. Pat. Nos. 4,683,195; 4,683,202; and 4,965,188. Commercial vendors, such as Perkin Elmer (Norwalk, Conn.), market PCR reagents and publish PCR protocols. For ease of understanding the advantages provided by the present invention, a summary of PCR is provided.

In each cycle of a PCR amplification, a double-stranded target sequence is denatured, primers are annealed to each strand of the denatured target, and the primers are extended by the action of a DNA polymerase. The process is repeated typically at least 25 times. The two primers anneal to opposite ends of the target nucleic acid sequence and in orientations such that the extension product of each primer is a complementary copy of the target sequence and, when separated from its complement, can hybridize to the other primer. Each cycle, if it were 100% efficient, would result in a doubling of the number of target sequences present.

Either DNA or RNA target sequences can be amplified by PCR. In the case of an RNA target, such as in the amplification of HCV genomic nucleic acid as described herein, the first step consists of the synthesis of a DNA copy (cDNA) of the target sequence. The reverse transcription can be carried out as a separate step, or, preferably, in a combined reverse transcription-polymerase chain reaction (RT-PCR), a modification of the polymerase chain reaction for amplifying RNA. The RT-PCR amplification of RNA is well known in the art and described in U.S. Pat. Nos. 5,322,770 and 5,310,652; Myers and Gelfand, 1991, *Biochemistry* 30(31):7661–7666; Copending U.S. patent application Ser. No. 08/240,547, now allowed; Young et al., 1993, *J. Clin. Microbiol.* 31(4):882–886; and Young et al., 1995, *J. Clin. Microbiol.* 33(3):654–657; each incorporated herein by reference.

Various sample preparation methods suitable for RT-PCR have been described in the literature. For example, techniques for extracting ribonucleic acids from biological samples are described in Rotbart et al., 1989, in *PCR Technology* (Erlich ed., Stockton Press, N.Y.) and Han et al., 1987, *Biochemistry* 2:1617–1625, both incorporated herein by reference. The particular method used is not a critical part of the present invention. One of skill in the art can optimize reaction conditions for use with the known sample preparation methods. Preferred sample preparation methods for use in the detection of HCV RNA are described in Copending U.S. patent application Ser. No. 08/240,547, now allowed; Young et al., 1993, supra, and Young et al, 1995, supra.

Due to the enormous amplification possible with the PCR process, low levels of DNA contamination from samples with high DNA levels, positive control templates, or from previous amplifications can result in PCR product, even in the absence of purposefully added template DNA. Laboratory equipment and techniques which will minimize cross contamination are discussed in Kwok and Higuchi, 1989, *Nature,* 339:237–238 and Kwok and Orrego, in: Innis et al. eds., 1990 PCR Protocols: A Guide to Methods and Applications, Academic Press, Inc., San Diego, Calif., which are incorporated herein by reference. Enzymatic methods to reduce the problem of contamination of a PCR by the amplified nucleic acid from previous reactions are described in PCT patent publication No. US 91/05210, U.S. Pat. No. 5,418,149, and U.S. Pat. No. 5,035,996, each incorporated herein by reference, and in Young et al., 1995, supra.

Amplification reaction mixtures are typically assembled at room temperature, well below the temperature needed to insure primer hybridization specificity. Non-specific amplification may result because at room temperature the primers may bind non-specifically to other, only partially complementary nucleic acid sequences, and initiate the synthesis of undesired nucleic acid sequences. These newly synthesized; undesired sequences can compete with the desired target sequence during the amplification reaction and can significantly decrease the amplification efficiency of the desired sequence. Non-specific amplification can be reduced using a "hot-start" wherein primer extension is prevented until the temperature is raised sufficiently to provide the necessary hybridization specificity.

In one hot-start method, one or more reagents are withheld from the reaction mixture until the temperature is raised sufficiently to provide the necessary hybridization specificity. Hot-start methods which use a heat labile material, such as wax, to separate or sequester reaction components are described in U.S. Pat. No. 5,411,876 and Chou et al, 1992, *Nucl. Acids Res.* 20(7):1717–1723, both incorporated herein by reference. In another hot-start method, a reversibly inactivated DNA polymerase is used which does not catalyze primer extension until activated by a high temperature incubation prior to, or as the first step of, the amplification (see copending U.S. patent application Ser. No. 60/002,673, filed Aug. 25, 1995, incorporated herein by reference). Non-specific amplification also can be reduced by enzymatically degrading extension products formed prior to the initial high-temperature step of the amplification, as described in U.S. Pat. No. 5,418,149, which is incorporated herein by reference.

Analysis of Amplified Product

In a preferred embodiment of the present invention, amplification of HCV genomic nucleic acid is carried out as part of an HCV detection assay. The amplification is carried out to increase the amount of HCV nucleic acid to a detectable level. Methods for detecting PCR amplified nucleic acids are well known in the art. For example, the presence and quantity of amplified product can be assayed directly using gel electrophoresis using protocols well known in the art (see, for example, Sambrook et al., 1989, supra).

Detection of the amplified product can be carried using oligonucleotide probes which hybridize specifically to the amplified HCV nucleic acid. Suitable protocols for detecting hybrids formed between probes and target nucleic acid sequences are known in the art. HCV nucleic acid amplified using the primers of Table 1 can be detected using the probes and methods described in Copending U.S. patent application Ser. No. 08/240,547, now U.S. Pat. No. 5,527,669 Young et al., 1993, supra; and Young et al, 1995, supra.

A preferred assay method, referred to as the 5'-nuclease assay, is described in U.S. Pat. No. 5,210,015 and Holland et al., 1991, *Proc. Natl. Acad. Sci. USA* 88:7276–7280, both incorporated herein by reference. In the 5'-nuclease assay, labeled detection probes are involved in the PCR amplification reaction mixture. The probes are modified so as to prevent the probes from acting as primers for DNA synthesis. Any probe which is hybridized to target DNA during a synthesis step, i.e., during primer extension, is degraded by the 5'-nuclease activity of the DNA polymerase, e.g., rTth DNA polymerase. The presence of degraded probe indicates both that hybridization between probe and target DNA occurred and that amplification occurred. Methods for detecting probe degradation are described in the '015 patent, and U.S. Pat. Nos. 5,491,063 and 5,571,673 both incorporated herein by reference, and in the examples, below.

The probe-based assay formats described above typically utilize labeled oligonucleotides to facilitate detection of the hybrid duplexes. Oligonucleotides can be labeled by incorporating a label detectable by spectroscopic, photochemical, biochemical, immunochemical, or chemical means. Useful labels include 32p, fluorescent dyes, electron-dense reagents, enzymes (as commonly used in ELISAS), biotin, or haptens and proteins for which antisera or monoclonal antibodies are available. Labeled oligonucleotides of the invention can be synthesized using the techniques described above.

An alternative method for detecting the amplification of HCV nucleic acid, in which the increase in the total amount of double-stranded DNA in the reaction mixture is monitored, is described in Higuchi et al., 1992, *Bio/Technology* 10:413–417; Higuchi et al., 1993, *Bio/Technology* 11:1026–1030; copending U.S. patent application Ser. No. 07/695,210, filed May 2, 1991; and European Patent Publication Nos. 487,218 and 512,334, each incorporated herein by reference. The detection of double-stranded target DNA relies on the increased fluorescence that ethidium bromide (EtBr) and other DNA binding labels exhibit when bound to double-stranded DNA. Amplification increases the amount of double-stranded DNA and results in a detectable increase in fluorescence. Because non-specific amplification and, in particular, primer-dimer, also results in the formation of double-stranded DNA, reduction of non-specific amplification is desirable. The primers of the present invention are particularly useful because they enable amplification with unexpectedly low levels of background non-specific amplification products.

The amplification methods and primers of the present invention are not limited to use in detection assays. For example, as is well known in the art, amplified nucleic acid can be used in cloning or sequencing (see, for example, U.S. Pat. No. 4,683,195). The present primers are useful in general due to the higher yields of amplified nucleic acid and lower level of non-specific amplification products obtained.

The present invention also relates to kits, multicontainer units comprising useful components for practicing the present method. A useful kit contains primers for the amplification of HCV nucleic acid. A kit can also contain means for detecting amplified HCV nucleic acid, such as oligonucleotide probes. Other optional components of the kit include, for example, an agent to catalyze the synthesis of primer extension products, substrate nucleoside triphosphates, appropriate buffers for amplification or hybridization reactions, and instructions for carrying out the present method. The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Amplification of HCV RNA

Amplifications of HCV RNA were carried out using the following protocol.

Sample Preparation

Amplifications were carried out both using synthetic RNA templates and using RNA isolated from clinical samples. The use of a synthetic template allowed control over the number of target RNA molecules added to each reaction. Synthetic RNA templates were transcribed using an HCV RNA transcription vector as described in Young et al., 1993, supra. For amplifications of HCV RNA from clinical samples, RNA was isolated from serum as described in Young et al., 1995, supra.

Amplification

Amplifications were carried out in 100 $\mu$l reactions volumes. Each reaction contained the following reagents:

HCV RNA template, 400 nM each primer (except where noted),

1 $\mu$M labeled probe, 50 mM Bicine (pH 8.3)

100 mM KOAc,

200 $\mu$M each dATP, dCTP, dGTP, and dUTP, 3.6 mM Mn(OAc)$_2$,

8% glycerol, 20 units of rTth DNA polymerase*, and 2 units of UNG*.

* manufactured and developed by Hoffmann-La Roche and marketed by Perkin Elmer, Norwalk, Conn.

A detection probe was included in each reaction mixture to enable detection of the amplified product using the 5'-nuclease assay, as described below. The probe used was KY150, described in copending U.S. patent application Ser. No. 08/240,547, now U.S. Pat. No. 5,527,669, and Young et al., 1995, supra. The probe was synthesized with fluorescein (FAM) (Perkin Elmer, Applied Biosystems Division, Foster City, Calif.) bound at the 5' end and a 3'-PO$_4$ instead of a 3'-OH to block any extension by the DNA polymerase.

Amplifications were carried out in a GeneAmp TC9600 DNA thermal cycler using thin-walled MicroAmp reaction tubes (both from Perkin Elmer, Norwalk, Conn.), using the following temperature profile:

Pre-reaction incubation 50° C. for 2 minutes;

Reverse transcription 60° C. for 30 minutes 2 cycles: denature 95° C. for 15 seconds, anneal/extend 60° C. for 20 seconds 46 cycles: denature 90° C. for 15 seconds, anneal/extend 60° C. for 20 seconds Hold 72° C. for no more than 15 minutes Following the temperature cycling, the reactions were held at −20° C. before analysis.

Detection of Amplified Product

Amplified HCV nucleic acid was analyzed both by gel electrophoresis and using the 5'-nuclease assay. Gel electrophoresis provided an easily visualized confirmation of the presence of amplified product and a rough estimate of the relative amount of amplification product produced. The 5'-nuclease assay was used to provide an accurate quantitative estimate of the amount of amplification product produced.

A. Gel Electrophoresis

The presence of amplified product was detected by gel electrophoresis as follows. Reaction products were fractionated using an agarose gel (3% NuSieve and 1% SeaChem) and 1X TBE (0.089 M Tris, 0.089 M boric acid, 0.0025 M disodium EDTA) running buffer. Electrophoresis was carried out at 100 volts for approximately 1 hour. Ethidium bromide (0.5 µg/ml) was added following electrophoresis to stain any DNA present. The gel was destained briefly in water and the ethidium bromide-stained bands of DNA were visualized using UV irradiation.

B. 5'-Nuclease Assay

As described above, amplifications were carried out in the presence of a fluorescein-labeled, HCV-specific detection probe modified so as to preclude extension by the DNA polymerase. The probe, which was complementary to a region of the HCV target sequence located between the two primer binding sites, was cleaved by the 5'-nuclease activity of the rTth DNA polymerase during primer extension. Following amplification, residual uncleaved probe was separated from reaction mixture and the fluorescence of the remaining cleaved probe fragments was then measured as an indication of the amount of amplification product synthesized.

Uncleaved probes were extracted from the reaction mixture following amplification using beads coated with polyethyleneimine (PEI), which bind to the full-length, uncleaved probe, but which do not bind appreciably to cleaved probe fragments. The PEI beads are added to the reaction mixture, allowed to bind to the uncleaved probes, and the resulting PEI-probe complexes are removed by centrifugation. The amount of probe cleavage fragments remaining is determined by measuring the fluorescence. Details of the PEI bead extraction are described below.

Prior to use, PEI beads (Baker Bond wide-pore PEI beads from J. T. Baker, Phillipsburg, N.J.) were soaked in distilled, deionized (dd) water at least for several hours (or overnight) at 4° C. The PEI beads were washed sequentially using the following: (1) dd water, (2) ethanol, (3) dd water, (4) 1M Tris (pH 8.3), (5) 50 mM Tris (pH 8.3), 1M NaCl, and (6) binding buffer (10 mM Tris, 50 mM KCl, 1 mM EDTA, 500 mM NaCl and 8 M Urea). After the last wash, the beads were resuspended in binding buffer at 60 mg (wet weight) of PEI beads per 300 pi of binding buffer.

To capture the unbound probe, 75 µl of the PCR reaction mixture were added to 300 µl of the PEI bead suspension (about 60 mg of PEI beads). The mixture was vortexed for 10 minutes to mix and allow binding of the PEI beads to the undegraded probes. Following centrifugation in a Microfuge at maximum speed for 2 minutes to remove the PEI-probe complexes, 200 pl1 of supernatent were transferred by pipette to the well of a microwell plate. The fluorescence was measured in a CytoFluor™ microtiter plate reader (Perceptive Biosystems, Bedford, Mass.) at room temperature using a 485 nm excitation filter (20 nm band pass width) and 530 nm emission filter (25 rim band pass width).

EXAMPLE 2

Comparison with Prior Art Primers—Analysis by Gel Electrophoresis

This example describes a comparison of the primers of the present invention to the primers described in the prior art which are most similar to the present primers. The property of the primers compared was the amplification efficiency, defined as the amount of product produced in a given number of amplification cycles.

The primers described in the prior art which are most similar to the primers of the present invention are KY80 (SEQ ID NO: 4) and KY78 (SEQ ID NO: 5) described in copending U.S. patent application Ser. No. 08/240,547, now U.S. Pat. No. 5,521,669; European Patent Publication No. 529,493; and Young et al., 1993, supra. A sequence comparison of these prior art primers and the primers of the present invention is provided below.

Comparison of Primer Sequences

| Upstream | Seq ID No. | |
|---|---|---|
| ST280A | 1 | 5'-GCAGAAAGCGTCTAGCCATGGCGTTA |
| KY80 | 4 | 5'-GCAGAAAGCGTCTAGCCATGGCGT |
| Downstream | | |
| ST778AA | 2 | 5'-GCAAGCACCCTATCAGGCAGTACCACAA |
| ST678A | 3 | 5'-GCAAGCACCCTATCAGGCAGTACCACA |
| KY78 | 5 | 5'-CTCGCAAGCACCCTATCAGGCAGT |

Amplifications were carried out as described in Example 1 using samples containing 0, 10, 25, and 100 copies of synthetic HCV RNA template. Reactions were carried out using the primer combinations shown below. Reactions (a), (b), and (c) contained 400 nM of each primer. Reaction (d) differed from (c) in that the primer concentrations were increased to 600 nM.
(a) KY80 (SEQ ID NO: 4) and KY78 (SEQ ID NO: 5) (b) KY80 (SEQ ID NO: 4) and ST778AA (SEQ ID NO: 2) (c) ST280A (SEQ ID NO: 1) and ST778AA (SEQ ID NO: 2) (d) ST280A (SEQ ID NO: 1) and ST778AA (SEQ ID NO: 2)

Amplifications with each primer pair and input target number were carried out in triplicate. The amplified products were analyzed by gel electrophoresis, as described above. The results are presented in FIG. 1. The bands corresponding to the amplified HCV target sequence are indicated; the lower bands corresponds to non-specific amplification products (primer dimer).

For each HCV target concentration, the most intense bands, corresponding to the greatest amount of amplification product, were produced using the primer pair ST280A (SEQ ID NO: 1) and ST778AA (SEQ ID NO: 2). Only this primer pair yielded a detectable amount of amplification product from 10 copies of target. Also apparent, particularly in the amplifications using 100 copies of target, is a significant decrease in amount of non-specific amplification product using ST280A (SEQ ID NO: 1) and ST778AA (SEQ ID NO: 2). A comparison of amplifications (c) and (d) indicates that a primer concentration of 400 nM provided better results than a primer concentration of 600 nM.

The amplifications carried out using KY80 (SEQ ID NO: 4) and ST778AA (SEQ ID NO: 2) were included to assess the improvement attributable to the RT primer of the present invention. The results obtained from amplifications (a) and (b) with 25 and 100 copies of the target sequence indicate that use of the RT primer of the present invention in combination with the prior art upstream primer resulted in a significant improvement in product yield, although not as great as obtained from amplifications (c) and (d) using a combination of both the RT and upstream primers of the present invention.

Although gel analysis provides easily visualized evidence of the superiority of the primers ST280A (SEQ ID NO: 1) and ST778AA (SEQ ID NO: 2), the intensity of the bands do not provide an accurate quantitative comparison of the amplification products. For a quantitative comparison, the 5'-nuclease assay was used.

EXAMPLE 3

Comparison with Prior Art Primers—5=-nuclease Analysis

This example describes amplifications using the primer combinations described in Example 2 wherein the analysis of the amplification products was carried out using the 5'-nuclease assay. Amplifications were carried out as described in Example 1 using samples containing 0, 10, 25, $10^2$, $10^3$, $10^4$, $10^5$, and $10^6$ copies of synthetic HCV RNA template and primer concentrations of 400 nM for each primer. Amplifications with each primer pair and input target number were carried out in triplicate. As in example 2, above, the following primer combinations were used.
(a) KY80 (SEQ ID NO: 4) and KY78 (SEQ ID NO: 5) (b) KY80 (SEQ ID NO: 4) and ST778AA (SEQ ID NO: 2) (c) ST280A (SEQ ID NO: 1) and ST778AA (SEQ ID NO: 2)

Figure 2:
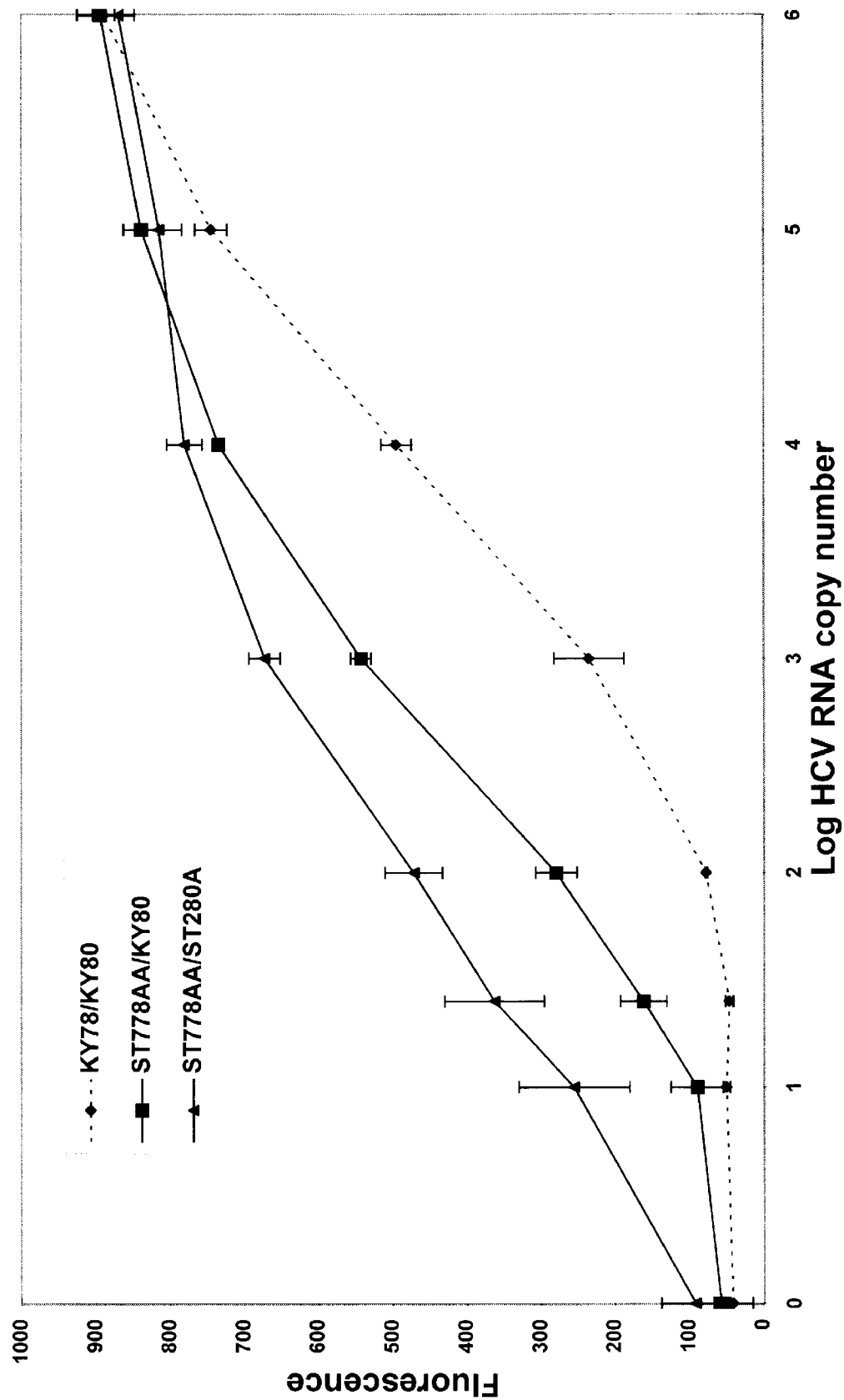
FIG. 2 provides the results of the amplifications described in Example 3.

The amplified product was analyzed using the 5'-nuclease assay, as described in example 1. The data are presented in FIG. 2, plotted as the fluorescence signal of the cleaved probe fragments versus the logarithm of the initial HCV target sequence copy number. Each fluorescence value is the average of the replicate measurements. The standard error for each value is indicated in FIG. 2.

The data presented in FIG. 2 provide confirmation of the significant improvement in amplification efficiency obtained using the primers of the present invention, as observed in the gel electrophoretic analysis presented in FIG. 1, described above. The fluorescence signals generated from amplifications of 10—$10^5$ copies of the target sequence using primer pair ST280A (SEQ ID NO: 1) and ST778AA (SEQ ID NO: 2) were significantly greater than the fluorescence signals generated from the corresponding amplifications using primer pair KY80 (SEQ ID NO: 4) and KY78 (SEQ ID NO: 5). Furthermore, as also seen in FIG. 1, amplifications using the RT primer of the present invention, ST778AA (SEQ ID NO: 2), in combination with the prior art upstream primer, KY80 (SEQ ID NO: 4), also resulted in a significant improvement in product yield, although not as great as obtained using a combination of both the RT and upstream primers of the present invention.

One measure of the relative amplification efficiency is provided by comparing the HCV input copy number required to obtain a given fluorescence signal. As seen in FIG. 2, the average signal obtained from the amplifications of 10 copies of HCV target using primer pair ST280A (SEQ ID NO: 1) and ST778AA (SEQ ID NO: 2) was approximately equal to the average fluorescence signal obtained from amplifications of $10^3$ copies of HCV using primer pair KY80 (SEQ ID NO: 4) and KY78 (SEQ ID NO: 5). Thus, a similar amount of amplification product was obtained from a 100-fold lesser input copy number, or, in other words, the amplifications using primer pair ST280A (SEQ ID NO: 1) and ST778AA (SEQ ID NO: 2) were about 100-fold more efficient than the amplifications using the prior art primers.

Another measure of the relative amplification efficiency is provided by comparing the lowest HCV target number detectable. Using primer pair ST280A (SEQ ID NO: 1) and ST778AA (SEQ ID NO: 2), amplifications of 10 copies of HCV RNA provided a clearly detectable signal. In contrast, using primer pair KY80 (SEQ ID NO: 4) and KY78 (SEQ ID NO: 5), amplifications of 10 copies of HCV target RNA did not result in a detectable signal. No detectable signal was generated using primer pair KY80 (SEQ ID NO: 4) and KY78 (SEQ ID NO: 5) below 100 copies of HCV.

Given the sequence similarity of the upstream primers ST280A (SEQ ID NO: 1) and KY80 (SEQ ID NO: 4), and the sequence similarity between the downstream primers ST778AA (SEQ ID NO: 2) and KY78 (SEQ ID NO: 5), there would be no reason to expect such a dramatic improvement in amplification efficiency. The observed improvement obtained using the primers of the present invention was surprising and unexpected in view of the prior art.

EXAMPLE 4

Comparison with Prior Art Primers: 5'-nuclease Assay

This example describes comparisons of amplifications using the following primer combinations.
(a) KY80 (SEQ ID NO: 4) and KY78 (SEQ ID NO: 5) (b) ST280A (SEQ ID NO: 1) and ST678A (SEQ ID NO: 3) (c) ST280A (SEQ ID NO: 1) and ST778AA (SEQ ID NO: 2)

Figure 3:
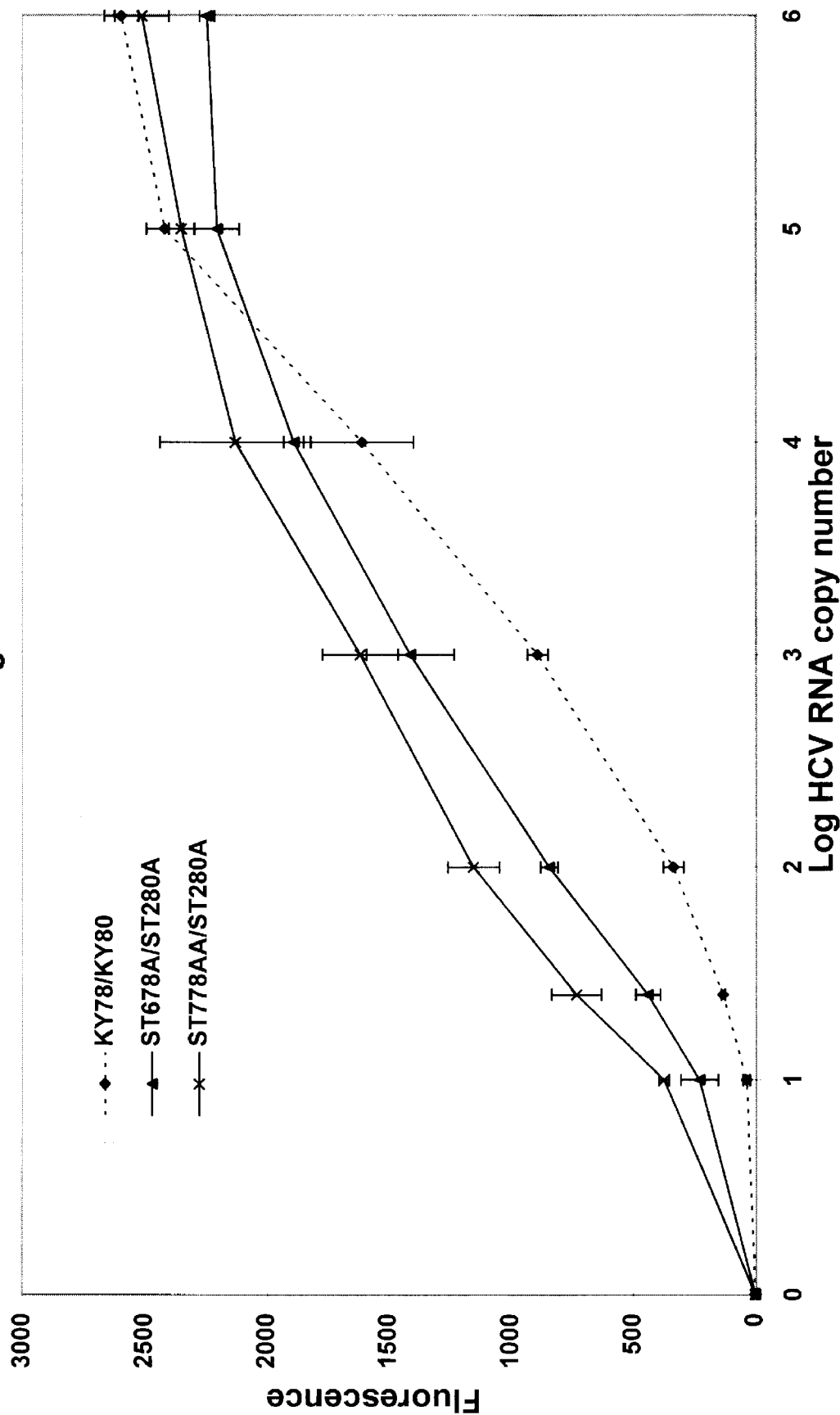
FIG. 3 provides the results of the amplifications described in Example 2.

Amplifications were carried out as described above using samples containing 0, 10, 25, $10^2$, $10^3$, $10^4$, $10^6$ and $10^7$ copies of synthetic HCV RNA template and primer concentrations of 400 nM for each primer. Amplifications with each primer set and input target number were carried out in triplicate. Amplified product was analyzed using the 5'-nuclease assay, as described above. The data are presented in FIG. 3, plotted as the fluorescence signal of the cleaved probe fragments versus the logarithm of the initial HCV target sequence copy number. Each fluorescence value is the average of the replicate measurements. The standard error of each value is indicated in FIG. 3.

The fluorescence signals generated from amplifications of 10–$10^4$ copies of target using either primer pair ST280A (SEQ ID NO: 1) and ST678A (SEQ ID NO: 3) or primer pair ST280A (SEQ ID NO: 1) and ST778AA (SEQ ID NO: 2) exceeded the fluorescence signals generated from the corresponding amplifications using primer pair KY80 (SEQ ID NO: 4) and KY78 (SEQ ID NO: 5). The results indicate that both primer pairs of the present invention amplified the HCV target RNA with greater efficiency than the prior art primers.

A comparison of the average signal obtained from amplifications of 10 copies of HCV target using primer pair ST280A (SEQ ID NO: 1) and ST778AA (SEQ ID NO: 2) to the average signal obtained from amplifications of 10² copies of HCV target using primer pair KY80 (SEQ ID NO: 4) and KY78 (SEQ ID NO: 5) shows that amplifications using primer pair ST280A (SEQ ID NO: 1) and ST778AA (SEQ ID NO: 2) were over 10-fold more efficient. Similarly, amplifications using primer pair ST280A (SEQ ID NO: 1) and ST678A (SEQ ID NO: 3) were nearly 10-fold more efficient within the same range of initial HCV target copy number.

EXAMPLE 5

Amplification in a Tricine Buffer

The 5'-nuclease assays described above used probes labeled with fluorescein (FAM) at the 5' end and a 3'-PO4 instead of a 3'-OH to block any extension by the DNA polymerase. Amplifications were also carried out using probes labeled with hexachlorofluorescein (HEX), also obtained from Perkin Elmer, Applied Biosystems Division (Foster City, Calif.). Unlike FAM-labeled probes, HEX-labeled probes were unstable in the Bicine amplification buffer described in example 1. However, HEX-labeled probes were found to be stable in Tricine amplification buffers.

Amplifications using Bicine and Tricine are essentially equivalent, although a routine reoptimization of the reagent concentrations is recommended. The reaction mixture found to be optimal for amplifications using a Tricine buffer is described below. No change of the temperature cycling was necessary.

HCV RNA template,
400 nM each primer,
1 $\mu$M HEX-labeled probe,
200 $\mu$M each dATP, dCTP, dGT?, and dUTP,
55 mM Tricine (pH 8.3),
90 mM KOAc,
3.0 mM $Mn(OAc)_2$,
8% glycerol,
20 units of rTth DNA polymerase*, and
2 units of UNG*.

* manufactured and developed by Hoffinann-La Roche and marketed by Perkin Elmer, Norwalk, Conn.

---

I claim:

1. An oligonucleotide primer for the polymerase chain reaction amplification of hepatitis C virus (HCV) nucleic acid, wherein said oligonucleotide primer is ST778AA (SEQ ID NO: 2).

2. A pair of oligonucleotide primers for the polymerase chain reaction amplification of hepatitis C virus (HCV) nucleic acid, wherein said pair is selected from the group consisting of ST280A (SEQ ID NO: 1) and ST778AA (SEQ ID NO: 2), ST280A (SEQ ID NO: 1) and ST678A (SEQ ID NO: 3), and KY80 (SEQ ID NO: 4) and ST778AA (SEQ ID NO: 2).

3. A pair of oligonucleotide primers of claim 2 consisting of ST280A (SEQ ID NO: 1) and STI778AA (SEQ ID NO: 2).

4. A pair of oligonucleotide primers of claim 2 consisting of ST280A (SEQ ID NO: 1) and ST678A (SEQ ID NO: 3).

5. A pair of oligonucleotide primers of claim 2 consisting of KY80 (SEQ ID NO: 4) and ST778AA (SEQ ID NO: 2).

6. A kit for detecting hepatitis C virus (HCV) nucleic acid, wherein said kit comprises a pair of oligonucleotide primers of claim 2.

7. A kit for detecting hepatitis C virus (HCV) nucleic acid, wherein said kit comprises a pair of oligonucleotide primers of claim 3.

8. A kit for detecting hepatitis C virus (HCV) nucleic acid, wherein said kit comprises a pair of oligonucleotide primers of claim 4.

9. A kit for detecting hepatitis C virus (HCV) nucleic acid, wherein said kit comprises a pair of oligonucleotide primers of claim 5.

10. A method for amplifying hepatitis C virus (HCV) nucleic acid, wherein said method comprises carrying out a polymerase chain reaction using a pair of oligonucleotide primers selected from the group consisting of ST280A (SEQ ID NO: 1) and ST778AA (SEQ ID NO: 2), ST280A (SEQ ID NO: 1) and ST678A (SEQ ID NO: 3), and KY80 (SEQ ID NO: 4) and ST778AA (SEQ ID NO: 2).

11. A method of claim 10, wherein said pair of oligonucleotide primers consists of ST280A (SEQ ID NO: 1) and ST778AA (SEQ ID NO: 2).

12. A method of claim 10, wherein said pair of oligonucleotide primers consists of ST280A (SEQ ID NO: 1) and ST678A (SEQ ID NO: 3).

13. A method of claim 10, wherein said pair of oligonucleotide primers consists of KY80 (SEQ ID NO: 4) and ST778AA (SEQ ID NO: 2).

14. A method for detecting hepatitis C virus (HCV) nucleic acid in a sample, comprising:
    (a) treating said sample in a polymerase chain reaction amplification mixture comprising a pair of oligonucleotide primers selected from the group consisting of ST280A (SEQ ID NO: 1) and ST778AA (SEQ ID NO: 2), ST280A (SEQ ID NO: 1) and ST678A (SEQ ID NO: 3), and KY80 (SEQ ID NO: 4) and ST778AA (SEQ ID NO: 2, under amplification conditions so that HCV nucleic acid, if present, is amplified; and
    (b) detecting if amplification has occurred, which indicates that HCV nucleic acid is present.

15. A method of claim 14, wherein said pair of primers consists of ST280A (SEQ ID NO: 1) and ST778AA (SEQ ID NO: 2).

16. A method of claim 14, wherein said pair of primers consists of ST280A (SEQ ID NO: 1) and ST678A (SEQ ID NO: 3).

17. A method of claim 14, wherein said pair of primers consists of KY80 (SEQ ID NO: 4) and ST778AA (SEQ ID NO: 2).

* * * * *